(12) United States Patent
Ten Kate (10) Patent No.: US 10,670,621 B2
(45) Date of Patent: Jun. 2, 2020

(54) FALL PREVENTION (71) Applicant: KONINKLIJKE PHILIPS N.V., Eindhoven (NL)

(72) Inventor: Warner Rudolph Theophile Ten Kate, Waalre (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 258 days.

(21) Appl. No.: 14/693,953

(22) Filed: Apr. 23, 2015

(65) Prior Publication Data
US 2015/0226764 A1 Aug. 13, 2015

Related U.S. Application Data (63) Continuation of application No. 13/377,419, filed as application No. PCT/IB2010/053090 on Jul. 6, 2010, now abandoned.

(30) Foreign Application Priority Data

Jul. 10, 2009 (EP) .................................... 09165127

(51) Int. Cl.
G01P 15/00 (2006.01)
A61B 5/11 (2006.01)
G08B 21/04 (2006.01)
A61B 5/00 (2006.01)
G01C 22/00 (2006.01)

(52) U.S. Cl.
CPC ............ *G01P 15/00* (2013.01); *A61B 5/1117* (2013.01); *A61B 5/7264* (2013.01); *A61B 5/7282* (2013.01); *G01C 22/006* (2013.01); *G08B 21/0446* (2013.01)

(58) Field of Classification Search
CPC ... G08B 21/0446; G01P 15/00; A61B 5/1117; A61B 5/112
See application file for complete search history.

(56) References Cited

U.S. PATENT DOCUMENTS

| 5,485,402 A | 1/1996 | Smith et al. |
| 5,836,887 A | 11/1998 | Oka et al. |
| 5,919,149 A * | 7/1999 | Allum .................. A61B 5/1116 600/595 |
| 6,305,221 B1 | 10/2001 | Hutchings |

(Continued)

FOREIGN PATENT DOCUMENTS

DE 1020050040861 A1 7/2006
EP 1195139 A1 4/2002

(Continued)

OTHER PUBLICATIONS

Ritchie, How to use Microsoft Excel as a Gradebook, University of Mississippi, Jun. 9, 2008.*

(Continued)

Primary Examiner — Kyle R Quigley (57) ABSTRACT

A fall risk of a user is determined by collecting measurements of the motion of the user. A value for a parameter related to the gait of the user is estimated from the measurements. The fall risk for the user is determined from a comparison of the estimated value with a normal value for the parameter determined from motion of the user in which the user is at their normal risk of falling.

13 Claims, 5 Drawing Sheets

(56) References Cited

U.S. PATENT DOCUMENTS

| | | | |
|---|---|---|---|
| 6,626,557 B1* | 9/2003 | Taylor | F21V 21/116 |
| | | | 362/235 |
| 7,610,166 B1 | 10/2009 | Solinsky | |
| 7,612,681 B2* | 11/2009 | Azzaro | A61B 5/1113 |
| | | | 340/573.1 |
| 8,206,325 B1* | 6/2012 | Najafi | A61B 5/1116 |
| | | | 600/587 |
| 2002/0143491 A1* | 10/2002 | Scherzinger | G01C 22/006 |
| | | | 702/160 |
| 2003/0228033 A1* | 12/2003 | Daniel | A61B 5/1038 |
| | | | 382/104 |
| 2005/0010139 A1 | 1/2005 | Aminian et al. | |
| 2005/0027216 A1 | 2/2005 | Guillemaud et al. | |
| 2006/0195050 A1 | 8/2006 | Alwan et al. | |
| 2007/0038155 A1 | 2/2007 | Kelly et al. | |
| 2007/0073514 A1 | 3/2007 | Nogimori et al. | |
| 2007/0112287 A1 | 5/2007 | Fancourt | |
| 2007/0143068 A1* | 6/2007 | Pasolini | G01C 22/006 |
| | | | 702/160 |
| 2008/0108913 A1 | 5/2008 | Lengsfeld et al. | |
| 2008/0133171 A1 | 6/2008 | Feichtinger et al. | |
| 2008/0146968 A1* | 6/2008 | Hanawaka | A61B 5/1038 |
| | | | 600/595 |
| 2009/0069724 A1 | 3/2009 | Otto et al. | |
| 2009/0079559 A1* | 3/2009 | Dishongh | A61B 5/1113 |
| | | | 340/539.13 |
| 2009/0240170 A1 | 9/2009 | Rowley et al. | |
| 2010/0286571 A1 | 11/2010 | Allum et al. | |

FOREIGN PATENT DOCUMENTS

| | | |
|---|---|---|
| FR | 2924847 A1 | 6/2009 |
| JP | 2002500768 A | 1/2002 |
| JP | 2006068300 A | 3/2006 |
| JP | 2007125368 A | 5/2007 |
| WO | 9944016 A1 | 9/1999 |
| WO | 2007033194 A2 | 3/2007 |
| WO | 2008059418 A | 5/2008 |
| WO | 2009021147 A1 | 2/2009 |
| WO | 2009071598 A1 | 6/2009 |
| WO | 2010026513 A1 | 3/2010 |

OTHER PUBLICATIONS

Weinberg: "Using the ADXLWOW in Pedometer and Personal Navigation Applications"; Analog Devices, AN-602 Application Note, 2002, 8 Page Document.

Zijlstra et al: "Displacement of the Pelvis During Human Walking: Experimental Data and Model Predictions"; Gait and Posture 6 (1997), pp. 249-262.

Hylton B. Menz et al: "A Structural Equation Model Relating Impaired Sensorimotor Function, Fear of Falling and Gait Patterns in Older People"; Gait & Posture, Elsevier LNKD-DOI:10.1016/J.Gaitpost 2006-04.005, vol. 25, No. 2, Jan. 5, 2007, pp. 243-249.

Hausdorff et al: Gait Variability and Fall Risk in Community-Living Older Adults: A 1-Year Prospective Study, Arch Phys Med Rehabil, vol. 82, Aug. 2001, pp. 1050-1056.

Luinge et al:: "Measuring Orientation of Human Body Segments Using Miniature Gyroscopes and Accelerometers"; Med. Biol. Eng. Comput., 2005, 43, pp. 273-282.

Willemsen et al: "Automatic Stance-Swing Phase Detection From Accelerometer Data for Peroneal Nerve Stimulation"; IEEE Transactions on Biomedical Engineering, vol. 37, No. 12, Dec. 1990, pp. 1201-1208.

* cited by examiner

FALL PREVENTION

This application is a continuation of U.S. application Ser. No. 13/377,419, filed Dec. 9, 2011, which application in turn is National Stage Entry of PCT/IB2010/053090, filed Jul. 6, 2010, which claims priority to European Application No. EP 09165127.3, filed Jul. 10, 2009.

TECHNICAL FIELD OF THE INVENTION

The invention relates to a method and device for monitoring the motion of a user, and in particular to a method and device for determining a fall risk for a user.

BACKGROUND TO THE INVENTION

Falls affect millions of people each year and result in significant injuries, particularly in the elderly. In fact, it has been estimated that falls are one of the top three causes of death in elderly people.

A fall is defined as a sudden, uncontrolled and unintentional downward displacement of the body to the ground. There are currently some fall detection systems available that detect these falls and allow the user to obtain assistance manually or automatically if a fall occurs. Exemplary fall detectors can comprise personal help buttons (PHBs) or worn and/or environment-based automatic detectors.

Automatic fall detectors comprise one or a set of sensors that measure the movement of the user, and a processor that compares the measured or processed signals with predetermined thresholds in order to detect a fall. In particular, automatic fall detectors store a set of predetermined threshold values and/or parameter sets. When the detector is activated, movement data obtained from the sensors (such as, for example, an accelerometer) will be continuously transformed and processed, and then compared with those parameter sets to determine if a fall event occurs.

Although these fall detectors are useful, they do not actually prevent falling, and only provide a warning or alarm in the event that a user already has fallen.

However, users that are insecure during walking, for example caused or enhanced by a fear of falling, by fatigue in the muscles, by frequently multi-tasking (i.e. they are carrying items when walking, talking to their grandchild, etc, or that move in places where there is dim lighting, a wet or irregular ground surface—such as loose carpet, electricity wires, toys, tools, and other hazards) or that are under medication that may affect balance or concentration, can be assisted by a device for fall prevention that decreases the actual risk of falling, or at least alerts the user that they are at a higher risk of falling at a particular time, and makes them feel more safe.

There is therefore a need for a method and device that can determine an instantaneous fall risk for a user.

SUMMARY OF THE INVENTION

According to a first aspect, there is provided a method of determining a fall risk of a user, the method comprising collecting measurements of the motion of the user; estimating a value for a parameter related to the gait of the user from the measurements; and determining a fall risk for the user from a comparison of the estimated value with a normal value for the parameter determined from motion of the user in which the user is at their normal risk of falling.

In a preferred embodiment, the step of determining a fall risk comprises weighting the comparison between the estimated value and the normal value according to a standard deviation of the normal value.

Preferably, the estimated value is determined from motion of the user over a period of time that is shorter than the period of time over which the normal value is determined.

In a preferred embodiment, the step of estimating comprises identifying a step boundary in the collected measurements.

In one embodiment, the step of identifying a step boundary comprises identifying clusters of contiguous measurements in the collected measurements in which the magnitude of each of the measurements exceeds a threshold.

In an alternative embodiment, the step of identifying a step boundary comprises identifying clusters of contiguous measurements in the collected measurements in which the magnitude of each of the measurements exceeds a threshold, apart from a subset of the measurements whose magnitude is less than the threshold, provided that the subset covers a time period less than a time threshold.

In another alternative embodiment, the step of identifying a step boundary comprises identifying clusters of contiguous measurements in the collected measurements, wherein the first collected measurement in the collected measurements whose magnitude exceeds a first threshold denotes the first measurement in a cluster and wherein the first collected measurement after the first measurement in the cluster whose magnitude falls below a second threshold denotes the last measurement in the cluster, provided that the last measurement is more than a minimum period after the first measurement.

In any of these alternative embodiments, the step of identifying step boundaries can further comprise identifying the step boundary as the measurement in each cluster with the highest magnitude.

In a preferred embodiment, the parameter related to the gait of the user comprises a step size and the step of estimating a value for the parameter comprises integrating horizontal components of the collected measurements with the integral bounds being given by consecutive identified step boundaries.

In a preferred embodiment, the step of estimating a value for the parameter comprises omitting the average velocity of the user from the integration such that the step size is determined based on the variation of the velocity.

In one embodiment, the parameter related to the gait of the user comprises, or additionally comprises, a forward step size and the step of estimating a value for the parameter comprises integrating horizontal components of the collected measurements with the integral bounds being given by consecutive identified step boundaries to give a start and end position for a step; and determining the forward step size as the norm of the vector connecting the start and end positions.

Preferably, the parameter related to the gait of the user additionally comprises a lateral step size and the step of estimating a value for the parameter further comprises defining a straight line between the start and end positions; integrating collected measurements occurring during the step to give a series of positions during the step; determining the distance between each position and the straight line; and determining the lateral step size as the maximum distance in this series.

In preferred embodiments, the method further comprises a calibration step that includes collecting measurements of the motion of the user when the user is at their normal risk of falling; and estimating the normal value for the parameter related to the gait of the user from the collected measurements.

Preferably, the step of estimating comprises estimating values for a plurality of parameters related to the gait of the user from the measurements, and the step of determining a fall risk comprises comparing the estimated values with values of the parameters determined from motion of the user in which the user is at a low risk of falling.

Preferably, the parameter or parameters related to the gait of the user is/are selected from step size, step width, step time, double support time, gait velocity, cadence, average step size, average step time, average double support time, average gait velocity and average cadence.

In accordance with a second aspect, there is provided a fall prevention device, comprising at least one sensor for collecting measurements of the motion of a user of the device; and a processor for estimating a value for a parameter related to the gait of the user from the measurements, and for determining a fall risk for the user from a comparison of the estimated value with a value of the parameter determined from motion of the user in which the user is at their normal risk of falling.

In accordance with a third aspect, there is provided a computer program product comprising computer-readable code that, when executed on a suitable computer or processor, is configured to cause the computer or processor to perform the steps in the method described above.

In accordance with alternative aspects, there are provided methods for determining gait parameters, including step boundaries, a step size, a forward step size and/or a lateral step size as described above and in the following Detailed Description.

BRIEF DESCRIPTION OF THE DRAWINGS

Embodiments of the invention will be described, by way of example only, with reference to the following drawings, in which.

DETAILED DESCRIPTION OF THE PREFERRED EMBODIMENTS

Although the invention will be described in terms of a method and device that is used for fall prevention, it will be appreciated that the method and device can be provided with additional functionality so that the device can also be used as a fall detector.

In a preferred embodiment, the fall prevention device comprises a single unit that is worn by a user.

Figure 1:
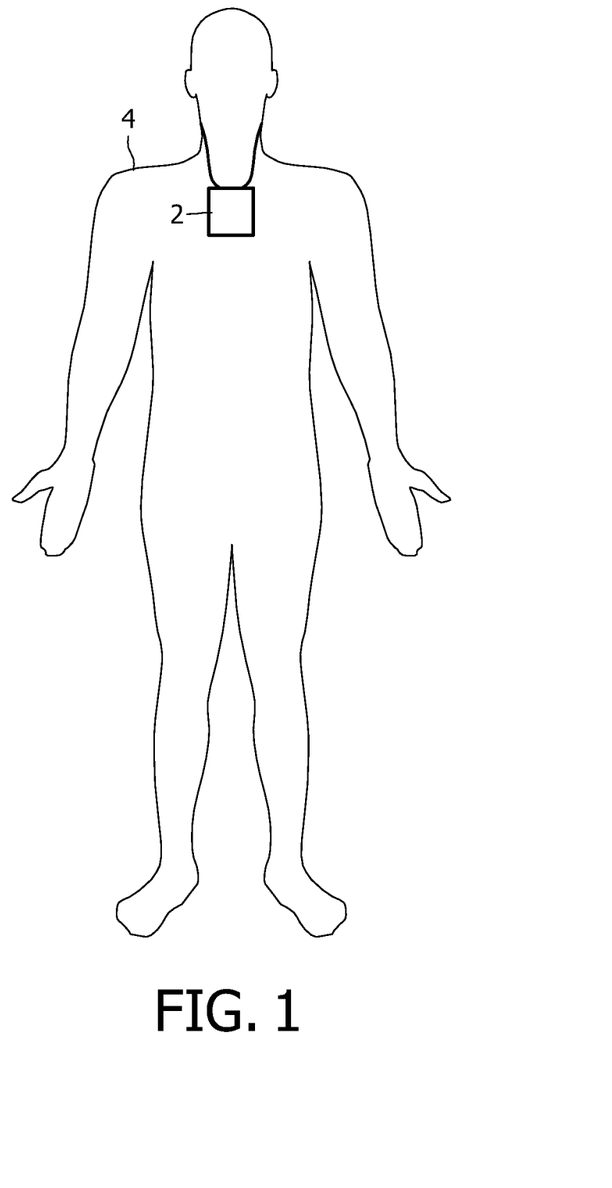
FIG. 1 shows a fall prevention device being worn by a user.
Figure 2:
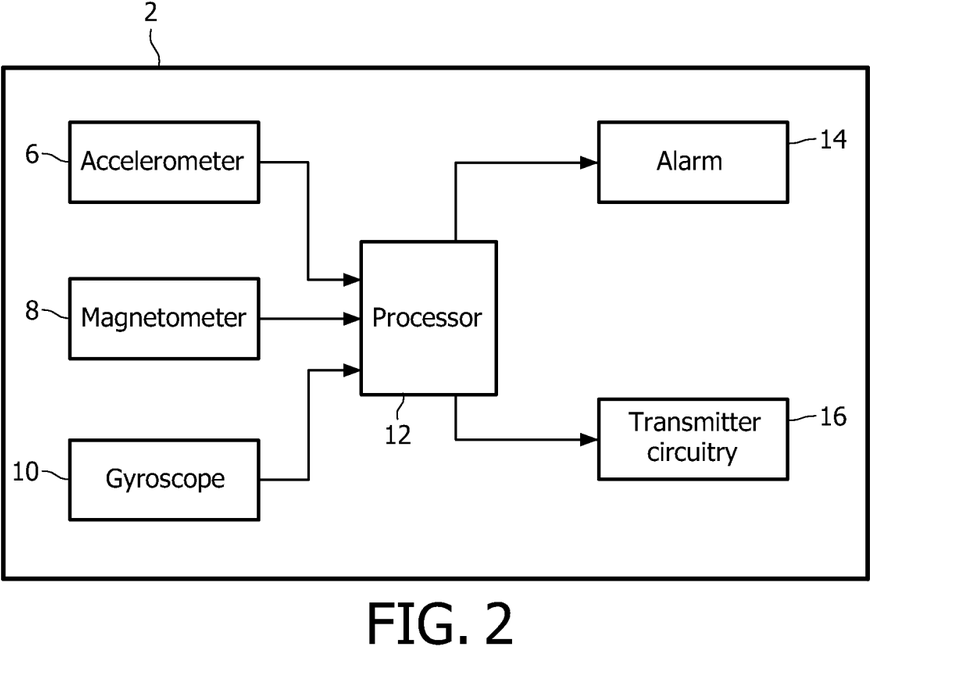
FIG. 2 shows the fall prevention device of FIG. 1 in more detail.

FIG. 1 shows a fall prevention device 2 in the form of a pendant being worn around the neck of a user 4 and FIG. 2 shows the fall prevention device 2 in more detail.

The fall prevention device 2 comprises three sensors, an accelerometer 6, a magnetometer 8 and a gyroscope 10, which are connected to a processor 12. The processor 12 receives measurements from the sensors 6, 8, 10 and processes the measurements to determine if the user 4 of the fall prevention device 2 is at a higher risk of falling.

In particular, the processor 12 processes the measurements from the accelerometer 6, magnetometer 8 and gyroscope 10 to determine the orientation of the fall prevention device 2, and processes the measurements from the accelerometer 6 (using the determined orientation) to determine parameters relating to the motion (and specifically the gait) of the user 2.

It should be understood that the three sensors are included by way of example only. Using sensor fusion, the measurements of the three sensors can complement each other for an optimal estimate of the orientation, as is known to those skilled in the art. Other sensors, for example a barometer and GPS receiver, can be added to further improve the accuracy of the parameters estimated by the device 2. It will be further appreciated that sensors can be omitted to reduce the power consumption and cost of the device 2—for example in a minimal device 2, only the accelerometer 6 is present, in which case it is only possible to estimate the inclination of the device 2.

The fall prevention device 2 also comprises an alarm 14 that can be activated by the processor 12 to warn or notify the user 4 that they are at an increased risk of falling. The alarm 14 can also comprise (or be replaced by) some means that provides the user 4 with an indication of their current risk of falling, even if they are not currently at a high risk of falling. For example, the fall prevention device 2 could be provided with means for providing vibrotactile or auditory feedback, or with a series of lights (or a light that can show different colors) which can be illuminated to indicate the current fall risk (for example there could be lights associated with the user 4 being at low, medium and high risk of falling).

The fall prevention device 2 also comprises transmitter circuitry 16 that allows the fall prevention device 2 to transmit an alarm or warning signal to a base station associated with the fall prevention device 2 (which can then issue an alarm or summon help from a healthcare provider or the emergency services). The base station can also carry out further processing of the sensor measurements, and/or store the sensor measurements for later analysis. In alternative embodiments, the transmitter circuitry 16 may be omitted if the fall prevention device 2 does not need to contact a base station to issue an alarm or summon help from a healthcare provider (for example if the fall prevention device 2 can contact the healthcare provider by using sound).

In some embodiments (not represented by the device 2 shown in FIG. 2), the fall prevention device 2 can include a memory unit for storing the sensor measurements for later analysis.

It is known that a large variance in gait parameters (i.e. parameters associated with the gait of a user) corresponds to a high risk of falling. However, this is a static relationship; the variance is an average obtained during general walking, and is related to an average risk of falling, which does not necessarily provide any information about the current risk of falling for the user 4. Gait parameters can include measures such as step size, step width, step time, double support time (i.e. the time that both feet are in contact with the ground), gait velocity, and cadence. The gait parameters can also include averages of the above measures over a few steps, so for example an average step size, average step width, average step time, average double support time, average gait velocity and average cadence.

The fall prevention device 2 determines values for gait parameters from sensor measurements covering a short period of time and compares these values with normal values for the user 4 (i.e. values that are obtained when the user 4 is at their normal (i.e. preferably a low or minimal) risk of falling). In particular, the fall prevention device 2 can determine various gait parameters from sensor measurements covering, say, 12 steps (so 6 strides). The normal values for the user 4 can be obtained by collecting measurements while the user 4 is walking steadily for a period of time (for example a minute) or for a certain number of steps (for example 40 steps).

Figure 3:
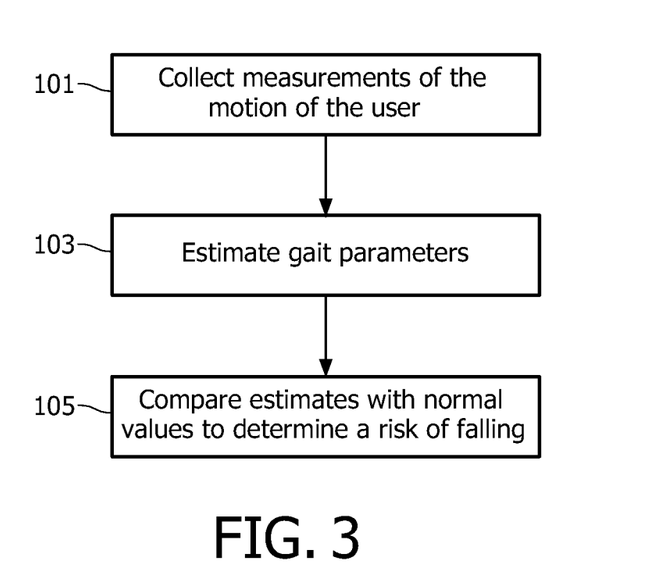
FIG. 3 is a flow chart illustrating the steps in a method according to the invention.

A method of determining a dynamic risk of falling is shown in FIG. 3. In step 101, the sensors 6, 8, 10 take measurements of the motion of the user 4 and in step 103, the processor 12 estimates values for the required gait parameters from the measurements. In step 105, the processor 12 then compares these estimates to usual values of these gait parameters for the user 4 to determine the user's dynamic risk of falling. As indicated above, the usual values correspond to those observed when the user 4 is at their normal (i.e. preferably a minimal or low) risk of falling.

The normal or usual values for the gait parameters can be obtained during a calibration session before the fall prevention device 2 is used (for example the user 4 can wear the fall prevention device 2 while it is in a calibration mode, and the fall prevention device 2 can determine values for each gait parameter while the user 4 is walking normally).

In a preferred embodiment, the comparison between the estimated values and the normal values is weighted according to the standard deviation of the normal gait parameter values.

For example, if $\mu$ represents the calibration mean (i.e. the mean of the normal values for a particular parameter), $\sigma$ represents the standard deviation in that calibration mean, and a represents the currently observed parameter value, a deviation is signaled if $$\frac{|a - \mu|}{\sigma} \quad (1)$$

exceeds a threshold.

For example, $$\exp\left[-\frac{(a - \mu)^2}{2\sigma^2}\right] \quad (2)$$

maps to a value between 0 and 1, where 1 indicates normal gait (for that user), and a deviation from normal gait is signaled (i.e. the user is at a higher risk of falling) if the result falls below a threshold, for example 0.7.

It will be appreciated that the values for $\mu$ and $\sigma$ are usually dependent on the user and will need to be set independently for each user.

In one embodiment, the processor 12 estimates values for an average step size and an average step width. However, in other embodiments, other combinations of gait parameters can be used.

The operation of the processor 12 in determining estimates for specific gait parameters will be described further below. As it will be shown, in the embodiment in which the fall prevention device 2 is a pendant located around the neck of the user 4, the way in which the averages a and $\mu$ are calculated relates them to the variance in step size rather than to the mean, as will be explained further below. Thus, the current and normal variances are effectively compared. It should be noted that a is typically averaged over a shorter period than $\mu$.

In addition, although in the preferred embodiment the fall prevention device 2 is in the form of a pendant to be worn around the neck of a user 4, it will be appreciated that it can be implemented in alternative forms that are to be worn on different parts of the body of the user 4, such as at the waist or on the ankle of the user 4. As described further below, in these embodiments, the processing used to determine the gait parameters from the sensor measurements.

Moreover, depending on the particular gait parameters that the processor 12 determines from the sensor measurements (and if the movements of the user 4 do not cause fast rotations of the fall prevention device 2), the gyroscope 10, the magnetometer 8 or both the magnetometer 8 and gyroscope 10 can be omitted from the device 2. In the embodiment in which the fall prevention device 2 is a pendant, it has been found that the gait variation estimate is less sensitive without the gyroscope 10, but it is still capable of detecting deviations from the normal gait.

Estimating the Step Size

In order to obtain an estimate of the step size, a number of processing steps are required. In particular, it is necessary to estimate the step boundaries and the orientation of the accelerometer (so that the accelerometer measurements can be transformed to Earth coordinates) in order to estimate the step or stride size.

Estimating step boundaries—It is important to accurately estimate step boundaries (which are defined as the moment of heel strike (HS), i.e. when the swing leg is touching the ground again, starting the stance phase), since missing a boundary will cause a significant deviation in a, hence leading to an alarm.

Step boundaries can also be used to estimate stepping time, which is another gait parameter, and, when combined with step size, allows an estimate of walking velocity to be determined.

For accelerometers that are rigidly attached to the upper body of a user, step boundaries are usually found by observing the 'zero' crossing of the vertical acceleration. Of course, it will be appreciated that the actual "crossing" will be through 1 g (9.81 ms$^{-2}$) since gravity is always acting on the user. The vertical acceleration will be known after the orientation of the accelerometer is determined—although for rigidly mounted accelerometers, the accelerometer reading along the coordinate axis corresponding to vertical usually provides a sufficient approximation.

However, in the preferred embodiment in which the fall prevention device 2 is in the form of a pendant, the fall prevention device 2 (and therefore the accelerometer 6) is free to move relative to the user 4, which means that the accelerometer coordinate system also moves relative to the user 4.

Figure 4:
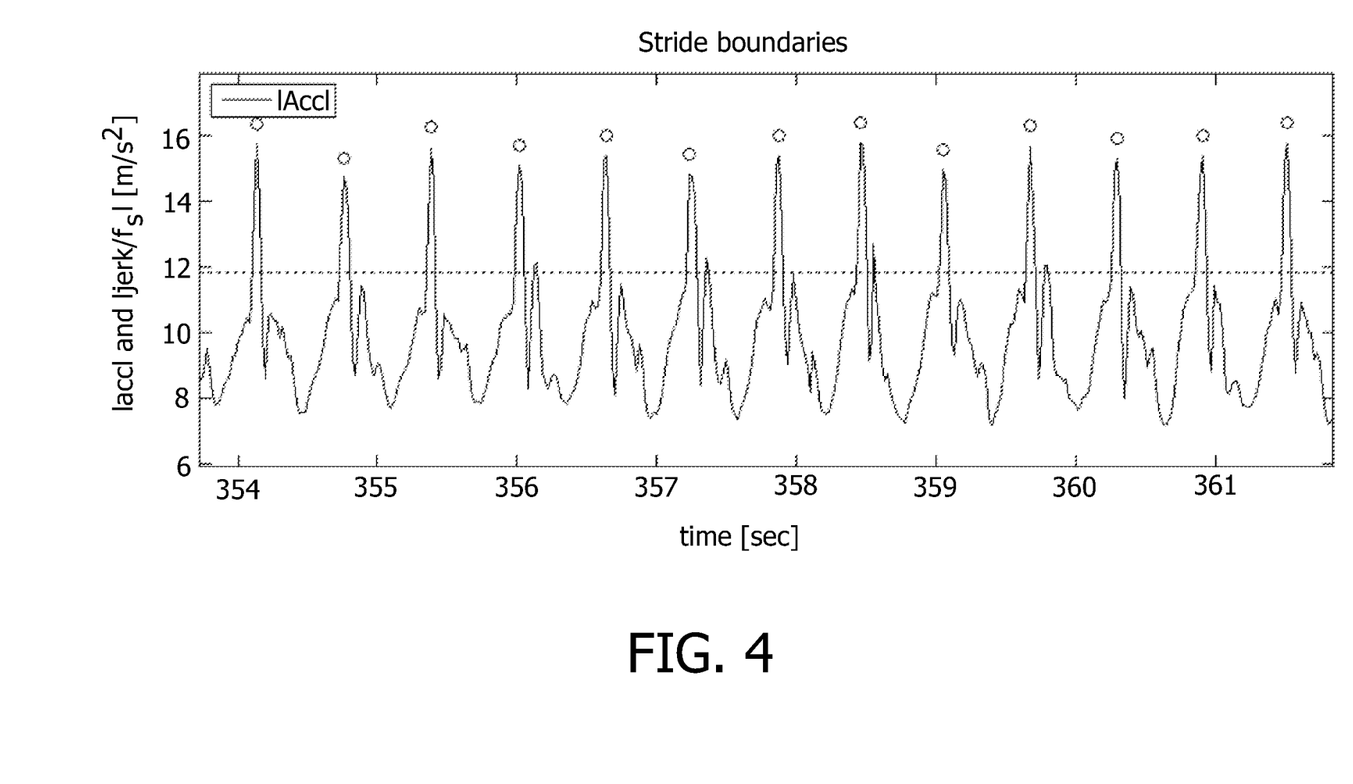
FIG. 4 is a plot illustrating measurements from an accelerometer that is in a pendant worn around a user's neck.

Therefore, it is preferred to modify the detection of step boundaries (i.e. heel strikes) as follows. Firstly, the norm of the signal from the accelerometer 6 is calculated. Then, the peaks in this signal serve as boundary markers for each step, which closely link to the heel strike (HS), as shown in FIG. 4.

The peaks are found using a two-step procedure. First, so-called clusters are identified. Second, the maximum value in each cluster is identified as the step boundary. The clusters are found as the range of samples that are above a certain threshold (typically 2 ms$^{-2}$ above gravity, i.e. ~12 ms$^{-2}$), where a small gap of samples not surpassing that threshold is permitted (typically 0.3 times a typical step time (which is around 0.5 seconds), i.e. 0.15 sec).

Figure 5:
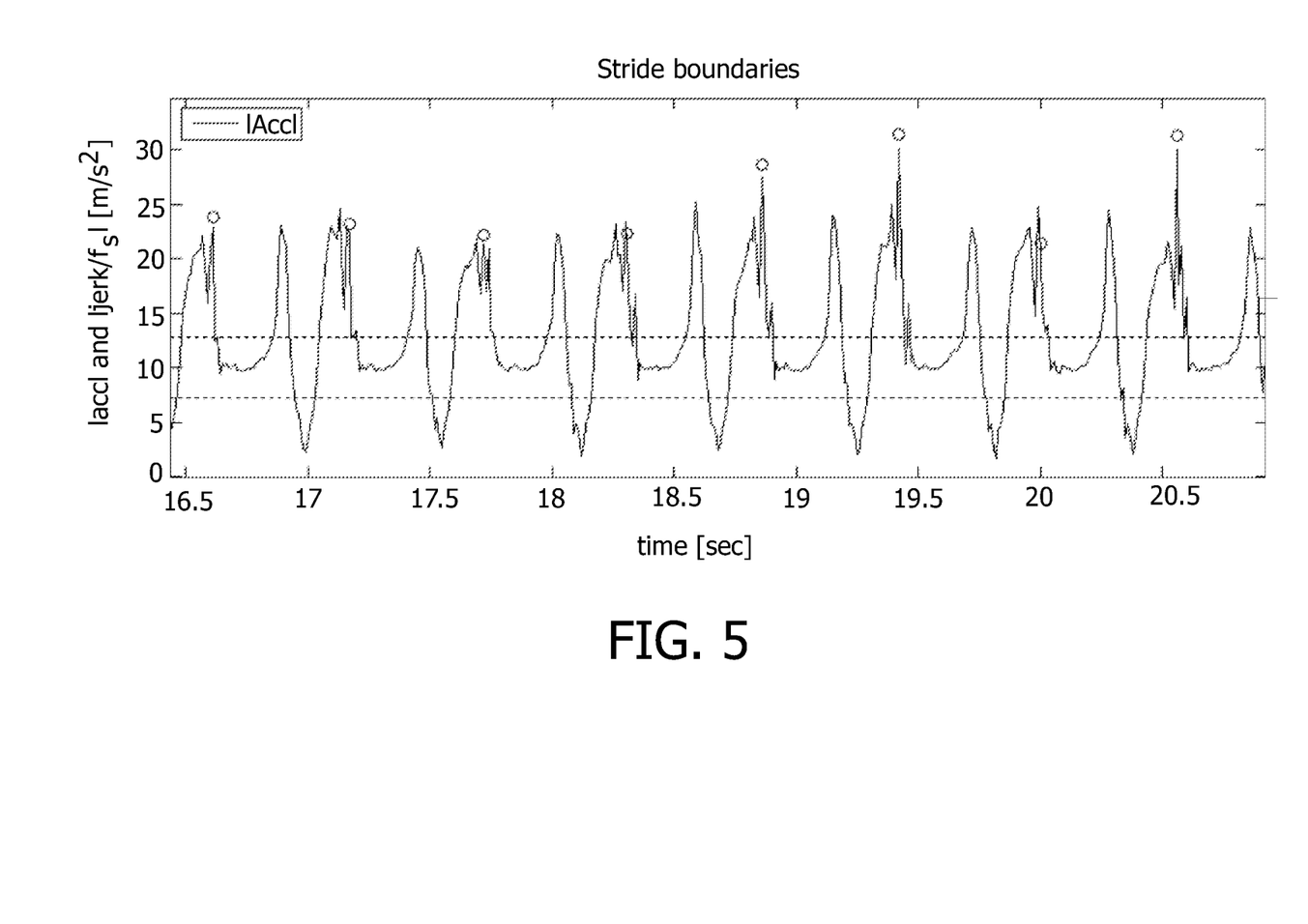
FIG. 5 is a plot illustrating measurements from an accelerometer that is worn on a user's ankle.

This algorithm works for accelerometers 6 that are attached to the upper body of the user 4. If the accelerometer 6 is attached at or to the lower body of the user 4 (for example the ankle), then usually two clusters appear per step, or actually per stride, as shown in FIG. 5. Since the accelerometer signal is observed at the ankle, the period of a stride (i.e. a step with both the left foot and the right foot) is seen.

One cluster corresponds to the lifting of the foot, and the other corresponds to the heel strike. It can be difficult to decide which of the two is the heel strike. However, it can also be observed that a single minimum occurs per step, and this can be used instead for detecting the step boundaries.

FIG. 5 also shows another way to identify the clusters. Instead of a single threshold (with a small gap being permitted), two thresholds are used. They introduce a hysteresis—surpassing one threshold indicates the start of a cluster, and falling below the second threshold indicates the end of a cluster, provided that the measurements fall below the second threshold after a minimum duration from the first measurement in the cluster. Preferably, the minimum duration is derived from the step time, as described above.

The unique minimum shown for each stride in FIG. 5 corresponds to the swing phase and it is less favorable to use this as the step boundary. Instead, it is preferable to use the heel strike as the step boundary for several reasons. Firstly, this is a clearly defined event. Secondly, when measuring at the feet or ankle, at heel strike the velocity relative to the ground is zero, which can be used in estimating the movement. Thirdly, at heel strike, the acceleration in the horizontal direction is low, which leads to lower errors when (double) integrating the acceleration for estimating the step size. The sample values at the beginning of the integration have a large influence on the outcome, so large values can cause a bias in the total outcome.

Figure 6:
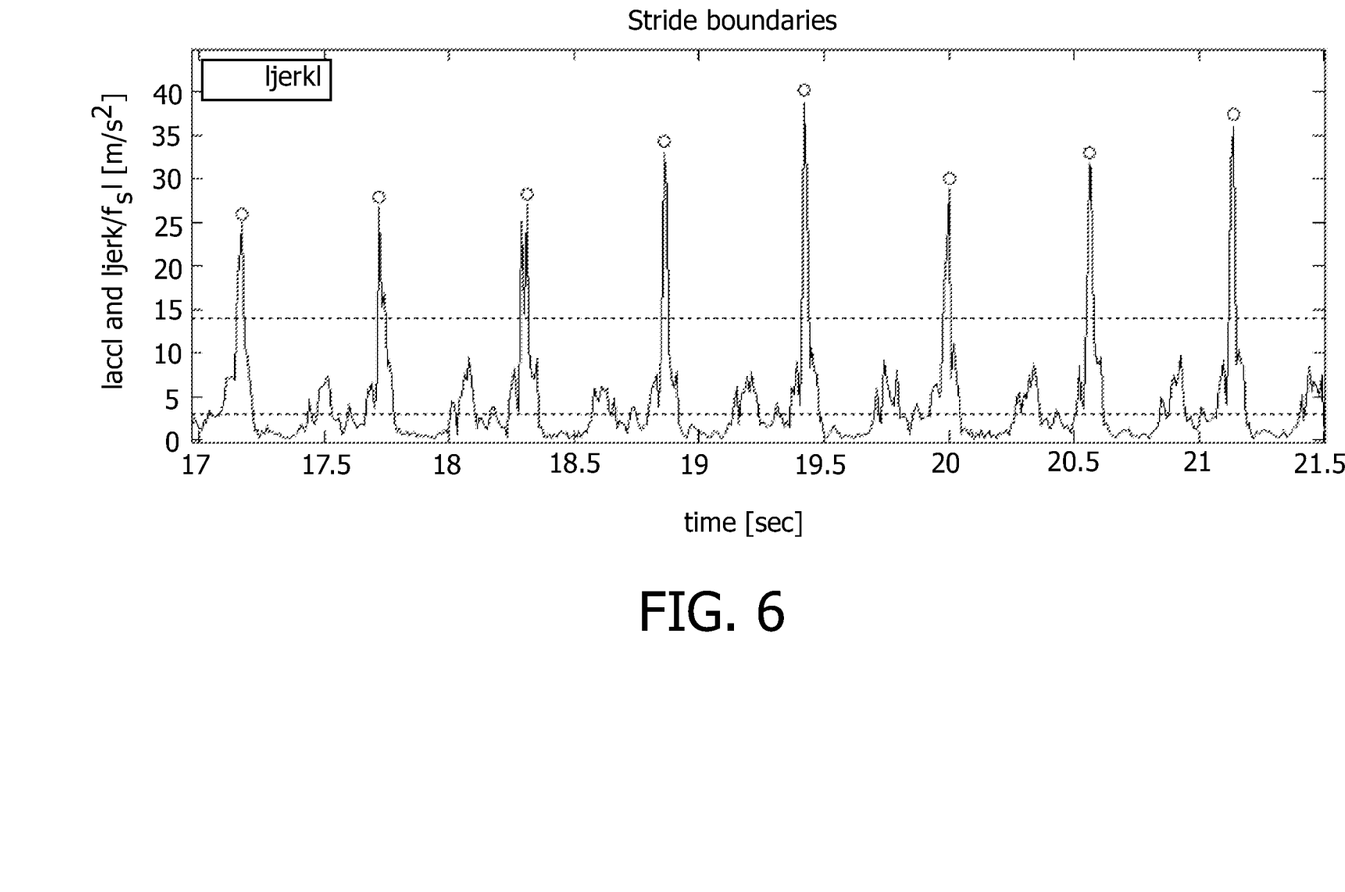
FIG. 6 is a plot illustrating the derivative of measurements from an accelerometer that is worn on a user's ankle.

A better algorithm for detecting step boundaries when the accelerometer 6 is located on the lower body of the user 4 is found by observing the derivative of the acceleration, as shown in FIG. 6. The boundaries are more clear, and they associate with the heel strike event.

It will be appreciated that as different algorithms can be used for different fall prevention device 2 locations on the user's body, the processor 12 in the fall prevention device 2 needs to know the location used. The user 4 may be able to select an appropriate location from a list of locations offered by the processor 12, or, alternatively, the processor 12 can execute a classifier algorithm to detect the location (and therefore the algorithm to use to detect the step boundary) based on the particular patterns in the measurements of the accelerometer 6.

Estimating accelerometer orientation—The orientation of the accelerometer 6 (and therefore the fall prevention device 2) can be estimated from the direction that gravity appears in the accelerometer coordinate system. By defining the z-axis to correspond with the vertical direction when the accelerometer 6 is not tilted, the orientation follows through the vector dot product of the measured gravity direction and the z-axis, i.e. through the z-component of the measured gravity (as is known, when using normalized values, the dot product equals the cosine of the enclosed angle).

Since the accelerometer 6 is sensitive to both acceleration due to gravity and acceleration due to movement, a filter is needed in order to estimate which component is due to gravity. Usually, a gyroscope 10 is added to measure the angular rotation speed and to correct the measured acceleration correspondingly. However, if the movements of the user 4 do not cause fast rotations of the fall prevention device 2, the gyroscope 10 can be omitted.

Without fast rotations, the gravity component can be found as the low-pass filtered component of the signal from the accelerometer 6. Since causality constraints in the filter design introduce a delay, the filtered acceleration signal needs to be corrected for this delay.

From the measured direction of gravity, the inclination or orientation of the fall prevention device 2 can be estimated. However, this inclination or orientation does not provide information about the horizontal direction of the device 2 (i.e. which way the device 2 is facing), so the magnetometer 8 can be used to determine the horizontal orientation of the device 2. Gyroscopes can also be used in the estimation of horizontal orientation.

Orientation can be expressed in different ways, of which Euler angles and Euler parameters are the most commonly used. They are usually implemented through matrices or quaternions. The algebras are isomorphic, and provide a way to transform the measured values (acceleration etc.) as expressed in the accelerometer's local coordinate system to the global (Earth) coordinate system.

Estimating step or stride sizes—Once the acceleration signals have been transformed to the Earth coordinate system, the step sizes can be computed by double integrating (with respect to time) the horizontal components of these transformed signals. The boundaries for the integrations are given by the estimated step boundaries. The integration constants, velocity and position at the beginning of the step, are both set to zero.

For the position this is fine, since the step size is needed, which is the difference between end and start position.

For the velocity this is correct in the case that the device 2 is located on a foot of the user 4, since upon heel strike the velocity relative to the Earth is zero. However, when the device 2 is located on the upper body of the user 4, for example when the device 2 is a pendant, there will be a near constant velocity. Therefore, setting the velocity to zero at each step boundary will introduce errors, since a constant velocity yields a larger step size estimate. However, if it is assumed that the velocity is constant during the period of observation, i.e. during the averaging period (typically around 10-12 steps for determining a, and around 30-60 seconds for determining μ), the constant velocity component can be omitted. This means that the step size can be computed based on the variation in the velocity, which means that the device 2 (and the estimated fall risk) will become independent of the current walking speed—only the deviations will be observed.

The step size p follows as the integral of velocity v over step time:

$$p = \int_{HS_0}^{HS_1} v \, dt = \bar{v}(HS_1 - HS_0) + \int_{HS_0}^{HS_1} \Delta v \, dt \qquad (3)$$

where $HS_0$ and $HS_1$ are the times of subsequent heel strikes (HS) and $\bar{v}$ and $\Delta v$ denote the average velocity and its deviation respectively.

Defining the step time $T = HS_1 - HS_0 = \bar{T} + \Delta T$, and $p = \bar{p} + \Delta p$, where $\bar{p} = \bar{v}\bar{T}$, the deviation in step size follows as:

$$\Delta p = \bar{v}\Delta T + \int_{HS_0}^{HS_1} \Delta v \, dt \qquad (4)$$

It should be noted that, by definition, the mean of $(\Delta p)^2$ equals the variance of p. The velocity deviation $\Delta v$ can be computed from the measured acceleration through:

$$\Delta v(t) = \Delta v(HS_0) + \int_{HS_0}^{t} a\, dt' \quad (5)$$

At constant walking velocity, $$\int_{HS_0}^{HS_1} a\, dt \approx 0 \quad (6)$$

and it is reasonable to assume that $\Delta v(HS_0)$ is roughly the same at each step. Then, by neglecting the first term in equation (4) above, $\Delta p$ is approximated as:

$$\Delta p \approx \int_{HS_0}^{HS_1} \Delta v(HS_0) dt + \int_{HS_0}^{HS_1} dt \int_{HS_0}^{t} a\, dt' = \Delta v(HS_0)(HS_1 - HS_0) + \int_{HS_0}^{HS_1} dt \int_{HS_0}^{t} a\, dt' = \mu + \Delta s \quad (7)$$

The second term, $\Delta s$, is the result of the double integration of the acceleration when using zero integration constants. Since, by definition, $E[\Delta p] = 0$, it follows that $$\mu = -E[\Delta s] \quad (8)$$

So, a first order approximation of $\mu$ can be obtained by observing the (horizontal) acceleration under stable walking conditions and computing the mean of the double integrated acceleration. This process also yields a standard deviation:

$$\mu_0 = \text{mean}(\Delta s_{stable}) \quad (9)$$

$$\sigma_0 = \text{std}(\Delta s_{stable}) \quad (10)$$

So, $\mu_0$ estimates $-\mu$, and the variance of p follows as $$\text{var}(p) = E[(\Delta p)^2] = \mu^2 + \mu_0^2 + \sigma_0^2 \quad (11)$$

In typical cases, $\sigma_0^2 \ll \mu_0^2$ and $\text{var}(p) \approx 2\mu^2$. During operation, a running estimate $a = E[\Delta s]$ is made over a few steps, and is compared with $\mu_0$ relative to $\sigma_0$, see equation (1). So, although mean values are compared, they basically reflect variance in the step sizes.

The values $\mu_0$ and $\sigma_0$ are user dependent and need to be set for each user in a calibration phase. Note, however, that since the average velocity $\bar{v}$ is not accounted for in the calculations, the method is insensitive to the actual walking speed of the user 4.

The first term $\bar{v}\Delta T$ in the expression for $\Delta p$ above has been neglected and introduces an error. It is proportional to the average velocity and the deviation in step time. As a refinement, it could be included in the estimate of $\Delta p$.

Since the orientation estimate contains errors, there is always some form of gravity leakage into the horizontal accelerations (i.e. the horizontal accelerations will include some component due to gravity) and double integration may induce large errors in the estimated step size. One way to suppress this leakage is by band-pass filtering (or high-pass filtering) the signals from the accelerometer 6, preferably using a linear phase filter so that the wave form of the signal is maintained. Typical cut-off frequencies are 0.1 Hz and 20-40 Hz (where the actual application of the upper cut-off frequency also depends on the used sampling frequency). This band-pass filtering is not required.

A measure that has been found to be particularly effective is the de-trending per integration interval (step or stride) of the acceleration. This amounts to requiring that the average acceleration (from the start heel strike to the end heel strike) is zero. In other words, the velocity after integration equals the velocity at the start of integration (which is zero). The de-trended acceleration is obtained by subtracting the integrated acceleration, divided by the step duration, from the measured acceleration. The de-trended acceleration is used to compute the step size as described above.

Assuming no errors in the coordinate system transformation, for example due to inhomogeneity in the direction and size of the geomagnetic field, this integration yields the direction of a step in terms of north-south and east-west. However, for gait stability it is necessary to examine the motion in forward and lateral directions. This is solved in the following way.

The start position (which is the origin, by definition) and the end position are computed as explained above. Their difference spans a 2D vector in the horizontal plane. Then, the forward step size is defined as the norm of this 2D vector, i.e. as the distance of the end position from the start position (it should be noted that, as a consequence, the above $\Delta p$ are always positive). Subsequently, a straight line is defined between the start position and the end position and the distance is determined between this line and each point from the double integration of the accelerometer measurements during the step. The maximum distance in this series is taken as the lateral step size.

Step time follows as the duration between the estimated step boundaries, and velocity as the ratio between step size and step time (in the event that the device 2 is located on a foot of the user 4).

While stride sizes are computed when the device 2 is on the lower body of the user 4, step size can be computed when the device 2 is on the upper body of the user 4, yielding twice as fast an average.

It will be appreciated by those skilled in the art that alternative methods for determining step size can be used that do not require the double integration of the horizontal acceleration measurements. These methods include the inverted pendulum model [Zijlstra & Hof, Displacement of the pelvis during human walking, Gait and Posture 6, 1997, 249-267] and the $4^{th}$ power root of the difference between maximum and minimum vertical acceleration [Weinberg, Using the ADXL202 in Pedometer and Personal Navigation Applications, Application Note AN-602, Analog Devices, 2002].

Although described in terms of a pendant to be worn around the neck of a user 4, it will be appreciated that the device can be worn on different parts of the body of the user 4. Of course, in these embodiments, the processing used to determine the gait parameters from the sensor measurements, but these modifications will be readily apparent to a person skilled in the art based on the description provided above.

In the embodiment described with reference to FIG. 2, the collection and processing of the sensor measurements is performed in a single unit. However, in alternative embodiments, the processing of the measurements can be performed in a unit that is remote from the sensors, in which case the fall prevention device 2 will comprise a sensor unit to be worn by the user 4 that transmits the sensor measurements to the remote unit. In this embodiment, there is no need for the sensor unit to include a dedicated processor.

There is therefore provided a method and device that can determine an instantaneous fall risk for a user.

It will be appreciated that the algorithms described above that are used to determine various gait parameters can be used in applications other than fall prevention. For example, they can be used in activity monitoring and fitness applications such as endurance coaching (for example to support the keeping of cadence during jogging). The algorithms may be used in step counters or devices that support injury prevention, for example during jogging. Further the algorithms may be used in a device or system that uses gait parameters as a biometric for identifying an individual.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall prevention device, comprising:
   at least one sensor configured to measure the motion of a user wearing the device;
   an alarm; and
   a processor programmed to:
   determine a value for one or more parameters related only to a gait of the user from the measurements, wherein the one or more parameters includes a forward step size and a lateral step size, and wherein the processor is further programmed to:
   integrate horizontal components of the received motion measurements with integral bounds being given by consecutive identified step boundaries to give a start and end position for a step;
   determine a norm of the vector connecting the start and end positions to the current value of the forward step size;
   define a straight line between the start and end positions;
   integrate collected motion measurements occurring during the step to give a series of positions during the step;
   determine a distance between each position of the series and the straight line; and
   determine a maximum distance of the series of positions as the lateral step size; and
   determine a fall risk for the user to trigger a warning of an increased risk of falling, wherein the fall risk is determined from a comparison of the value with a normal value for the one or more parameters determined from motion of the user in which the user is at a normal risk of falling, wherein the determination of the fall risk further comprises:
   receive motion measurements over a first period of time when the user is walking normally;
   determine a mean $\mu$ of values for the one or more parameters from the motion measurements over the first period of time;
   determine a standard deviation $\sigma$ of the mean $\mu$;
   receive motion measurements subsequent to the first period of time;
   determine a current value a of the one or more parameters from the motion measurements received subsequent to the first period of time;
   periodically calculate $$\frac{|a - \mu|}{\sigma}$$

subsequent to the first period of time; and
   in response to $$\frac{|a - \mu|}{\sigma}$$

exceeding a preselected threshold, trigger the warning by activating the alarm to indicate the increased risk of falling.

2. The device of claim 1, wherein the one or more parameters includes both average forward direction step length and average lateral direction step width over the first period of time and a second period of time, and wherein the second period of time is shorter than the first period of time.

3. The device of claim 1, wherein the one or more parameters includes step length and the processor is further programmed to:
   when the user is walking, identify clusters in the motion measurements exceeding a threshold;
   from the clusters, determine step boundaries;
   from the step boundaries, determine lengths of a plurality of steps; and
   average the lengths to calculate the current value a.

4. The device of claim 3, wherein the processor is programmed to identify the step boundaries as the motion measurement in each cluster with the highest magnitude.

5. The device of claim 3, wherein the one or more parameters of the user comprises a step size and the processor is further programmed to:
   compute a double integration with respect to time of horizontal acceleration components of the received motion measurements to determine the length of each step.

6. The device of claim 1, wherein the processor is configured to estimate the value for the one or more parameters of the user by identifying a step boundary in the collected measurements by:
   identifying clusters of contiguous measurements in the collected measurements in which the magnitude of each of the measurements exceeds a threshold;
   identifying clusters of contiguous measurements in the collected measurements in which the magnitude of each of the measurements exceeds a threshold apart from a subset of the measurements whose magnitude is less than the threshold, provided that the subset covers a time period less than a time threshold; or
   identifying clusters of contiguous measurements in the collected measurements, wherein the first collected measurement in the collected measurements whose magnitude exceeds a first threshold denotes the first measurement in a cluster and wherein the first collected measurement after the first measurement in the cluster whose magnitude falls below a second threshold denotes the last measurement in the cluster, provided that the last measurements is more than a minimum period after the first measurement.

7. A method of determining a fall risk of a user using a device comprising one or more motion measuring sensors and one or more processors, the method comprising:

with the one or more motion measuring sensors, collecting measurements of motion of the user;
with the one or more processors:
estimating a value for one or more parameters related only to a gait of the user from the measurements, wherein the one or more parameters comprises a forward step size and a lateral step size, further comprising:
integrating horizontal components of the received motion measurements with integral bounds being given by consecutive identified step boundaries to give a start and end position for a step;
determining a norm of the vector connecting the start and end positions to the current value of the forward step size;
defining a straight line between the start and end positions;
integrating collected motion measurements occurring during the step to give a series of positions during the step;
determining a distance between each position of the series and the straight line; and
determining a maximum distance of the series of positions as the lateral step size; and
determining a fall risk for the user to trigger a warning of an increased risk of falling, wherein the fall risk is determined from a comparison of the estimated value with a normal value for the one or more parameters determined from motion of the user in which the user is at a normal risk of falling, wherein the determining further comprises:
receiving motion measurements over a first period of time when the user is walking normally;
determining a mean $\mu$ of values for the one or more parameters from the motion measurements over the first period of time;
determining a standard deviation $\sigma$ of the mean $\mu$;
receiving motion measurements subsequent to the first period of time;
determining a current value a of the one or more parameters from the motion measurements received subsequent to the first period of time;
periodically calculating $$\frac{|a-\mu|}{\sigma}$$

subsequent to the first period of time; and
in response to $$\frac{|a-\mu|}{\sigma}$$

exceeding a preselected threshold, triggering the warning by activating an alarm to indicate the increased risk of falling.

8. The method of claim 7, wherein estimating the value of the one or more parameters includes:
identifying a step boundary by identifying clusters of contiguous measurements in the collected measurements in which at least one of:
a magnitude of each of the measurements exceeds a threshold;
a magnitude of each of the measurements exceeds a threshold, apart from a subset of the measurements whose magnitude is less than the threshold, provided that the subset covers a time period less than a time threshold; and
wherein the collected measurements whose magnitude exceeds a first threshold denotes a first measurement in a cluster and a first collected measurement after the first measurement in the cluster whose magnitude falls below a second threshold denotes a last measurement in the cluster, and in which the last measurement is more than a minimum period after the first measurement.

9. The method of claim 7, wherein the one or more parameters includes a step length and further including with the one or more processors:
when the user is walking, identify clusters in the motion measurements exceeding a threshold;
from the clusters, determining step boundaries;
from the step boundaries, determining lengths of a plurality of steps; and
averaging the lengths to calculate the current value a.

10. The method of claim 8, wherein the one or more parameters comprises a step size and the step of estimating a value for the one or more parameters comprises computing a double integration with respect to time of the horizontal components of the collected measurements relating to acceleration with integration constants being set to zero at the beginning of the step.

11. The method of claim 8, wherein the one or more parameters includes forward step size and the step of estimating a value for the one or more parameters comprises:
integrating horizontal components of the collected measurements with the integral bounds being given by consecutive identified step boundaries to give a start position and an end position for a step; and
determining the forward step size as a norm of a vector connecting the start and end positions.

12. A method of determining a fall risk of a user using a device comprising one or more motion measuring sensors and one or more processors, the method comprising:
with the one or more motion measuring sensors, collecting measurements of motion of the user;
with the one or more processors:
estimating a value for one or more parameters related to a gait of the user from the measurements, wherein estimating the value of the one or more parameters includes:
identifying a step boundary by identifying clusters of contiguous measurements in the collected measurements in which at least one of:
a magnitude of each of the measurements exceeds a threshold;
a magnitude of each of the measurements exceeds a threshold, apart from a subset of the measurements whose magnitude is less than the threshold, provided that the subset covers a time period less than a time threshold; and
wherein the collected measurements whose magnitude exceeds a first threshold denotes a first measurement in a cluster and a first collected measurement after the first measurement in the cluster whose magnitude falls below a second threshold denotes a last measurement in the cluster, and in which the last measurement is more than a minimum period after the first measurement;
wherein the one or more parameters comprises a step size and the step of estimating a value for the one or more parameters comprises computing a double integration with respect to time of the horizontal components of the collected measurements relating to acceleration with integration constants being set to zero at the beginning of the step;

wherein the one or more parameters comprises a lateral step size and the step of estimating a value for the one or more parameters further comprises: defining a straight line between the start and end positions; integrating collected measurements occurring during the step to give a series of positions during the step; determining the distance between each position and the straight line; and determining the lateral step size as the maximum distance in this series; and determining a fall risk for the user, wherein the fall risk is determined from a comparison of the estimated value with a normal value for the one or more parameters determined from motion of the user in which the user is at a normal risk of falling.

13. A fall prevention device, comprising:

at least one sensor configured to measure the motion of a user wearing the device; and a processor programmed to:

determine a value for one or more parameters related only to a gait of the user from the measurements; and determine a fall risk for the user to trigger a warning of an increased risk of falling, wherein the fall risk is determined from a comparison of the value with a normal value for the one or more parameters determined from motion of the user in which the user is at a normal risk of falling, wherein the one or more parameters includes both average forward direction step length and average lateral direction step width over a first period of time when the user is walking normally and a second period of time, and wherein the second period of time is shorter than the first period of time.

* * * * *